Figure 1:
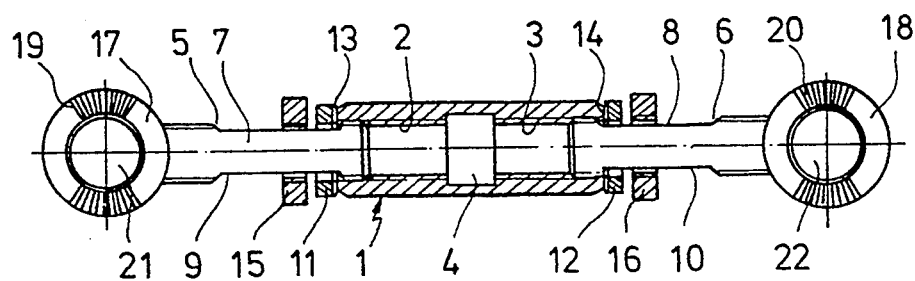

United States Patent
Metz-Stavenhagen

Patent Number: 5,413,602
Date of Patent: May 9, 1995

[54] VERTEBRAL BODY SPACER DEVICE

[75] Inventor: Peter Metz-Stavenhagen, Bad Wildungen, Germany

[73] Assignee: Howmedica GmbH, Schoenkirchen, Germany

[21] Appl. No.: 953,164

[22] Filed: Sep. 29, 1992

[30] Foreign Application Priority Data

Sep. 30, 1991 [DE] Germany .......... 91 12 176.0 U

[51] Int. Cl.⁶ ............................................. A61F 2/44
[52] U.S. Cl. ................................. 623/17; 606/60; 606/61
[58] Field of Search ............... 623/17; 606/53, 60, 606/61

[56] References Cited

U.S. PATENT DOCUMENTS

| | | | |
|---|---|---|---|
| 4,553,273 | 11/1985 | Wu | 606/61 X |
| 4,657,550 | 4/1987 | Daher | 623/17 |

FOREIGN PATENT DOCUMENTS

| | | | |
|---|---|---|---|
| 0188954 | 7/1986 | European Pat. Off. | |
| 3729600 | 3/1989 | Germany | 623/17 |
| 4109941 | 10/1992 | Germany | 623/17 |

Primary Examiner—Randall L. Green
Assistant Examiner—Dinh X. Nguyen
Attorney, Agent, or Firm—Peter C. Richardson; Lawrence C. Akers; Elizabeth O. Slade

[57] ABSTRACT

A spacer device for supporting vertebral bodies, comprising a first supporting member to engage a first vertebral body, a second supporting member to engage a second vertebral body and an adjustment means including a sleeve having an internal thread and a pair of bolts each having an outer thread cooperating with said sleeve to adjust the supporting members in a predetermined distance with respect to each other, whereby the adjustment means is provided with clamping faces at either end, which adjustment faces are aligned with the axis of the sleeve and the bolts or alternatively are disposed parallel to said axis, the supporting members are provided with clamping faces extending substantially normally with respect to the supporting faces and a screw connection is provided for each supporting member to press the clamping faces of the adjustment means and the supporting member together in a predetermined position with respect to each other. The first and second supporting members are preferably plate shaped and in the shape of vertebral discs and have prongs which engage natural vertebral discs.

22 Claims, 1 Drawing Sheet

VERTEBRAL BODY SPACER DEVICE

The present invention relates to a vertebral body spacer device.

A spacer of the type referred to is suited to fix a pair of vertebral bodies in a constant distance from each other after at least a vertebral body therebetween has to be removed, for example due to cancer. For further bridging the distance between the vertebral bodies, autologic bone chips or, respectively, an alloplastic substitute can be additionally incorporated.

European patent application 0 328 883 teaches a supporting means for the human vertebral column, comprising a pair of threaded bolts, which are inserted in both sides of a threaded sleeve. The bolt heads are provided with clamping faces cooperating with corresponding clamping faces of pedicel screws and screwed connections for fixing the position of the pedicel screws at the threaded bolts. The sleeve and bolts define an adjusting means to fix the distance of the pedicel screws and thus of the vertebral bodies receiving said pedicels. The adjusting means is positioned outside of the vertebral column so that it is subjected to relatively deleterious static and dynamic loads when used for bridging missing vertebras. Producing this device is also costly to obtain the safety required.

German patent 30 23 942 teaches an implant to be inserted between vertebra bodies. Again an adjusting means comprises a threaded sleeve and bolts at either end of the sleeve, the bolts including supporting members formed as discs and projections cooperating with the inner faces of the vertebra bodies to be fixed in a relative position with respect to each other. This structure provides for an improvement in taking up the load when compared with the pedicel screw apparatus referred to above, however, it is adjustable only along the longitudinal axis of the sleeve. Furthermore, adjustment is limited, as the threaded bolts and the sleeve interengage in sections only because of their oval-shaped cross-section. A tilting of the vertebras supported relative to each other is not possible, but is desired for certain regions of the vertebral column when deformations have been developed.

The same applies for the implant according to German patent 37 29 600 disclosing supporting members having an angular profile to abut against the faces of the vertebral bodies to be supported to be screwed thereon. For adjusting the supporting members, the passages for the bone screw are formed as elongated bores. Readjusting the implant is rather limited and difficult to perform, in as much additional thorns are provided for fixing the supporting member.

Still further, German petty patent 91 01 603 teaches a vertebral implant incorporating supporting faces which are adjustable relative to each other by threaded bolts, wherein the longitudinal length is variable by means of insertable spacer means. This type of implant is costly in constructing and keeping on stock and there is one degree of freedom only to adjust the supporting faces.

Therefore it is the object of the present invention to provide a vertebra body spacer substantially improving the adjustment with respect to the vertebra bodies to be supported and which can be placed on stock more easily.

According to the present invention the spacer is provided with an improved adjusting means by providing the clamping faces to connect the adjusting means to the supporting members. The supporting faces thus can be tilted relative with respect to the axis of the sleeve and screw bolts, wherein the relative rotation of bolts and sleeves allows for a tilting motion in any abitrary direction. The axial displacement of the supporting faces relative to each other due to the threaded engagement between the bolts and the sleeve which is inherent to the device is very small and can be easily accepted. Moreover, the spacer means of the invention allows to use components of pedicel screw devices according to European application 0 328 883 such as the sleeve and bolts including clamping faces as well as correlated fixing means, as this technique is at least mainly used for vertebral corrections.

According to the invention, the supporting members are additionally provided with clamping faces resulting in the advantage that in contrast to conventional spacers, the system is compatible with pedicel screw systems. When replacing a single vertebra only, the short vertebral distance is bridged by short sleeves and bolts.

Providing a sleeve and a pair of bolts improves varying the supporting member adjustment in the axial as well as tilting direction. The safety of the vertebral support is improved by the friction or, respectively the positive engagement of the clamping faces. The sleeve is provided with tool receiving faces to facilitate adjusting. Fixing means acting between the bolts and the sleeve, in particular including a disc, improve the support in the axial direction.

When the supporting members are formed as supporting plates, the axial length is decreased so that the space may be used when even a single vertebra is removed. The plates may be formed round or oval shaped to better fit to the shape of the vertebra bodies to be supported. Pins extending from the plates facilitate the anchorage in the vertebral bodies. The pin ends are rounded to facilitate the penetration in the relatively soft vertebral material.

Figure 2:
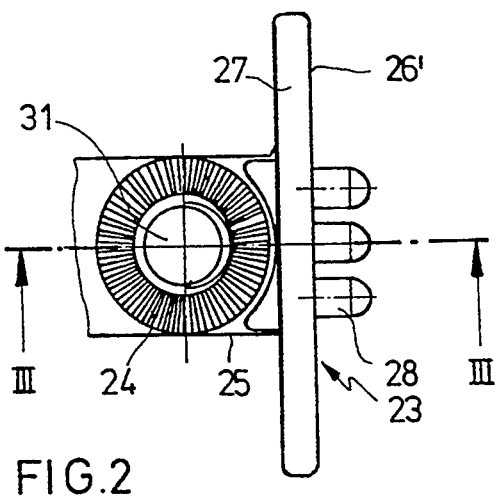
Figure 3:
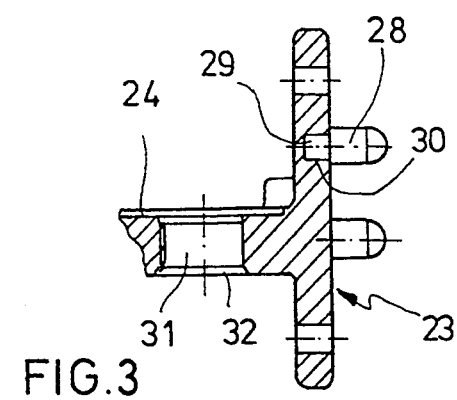
Figure 4:
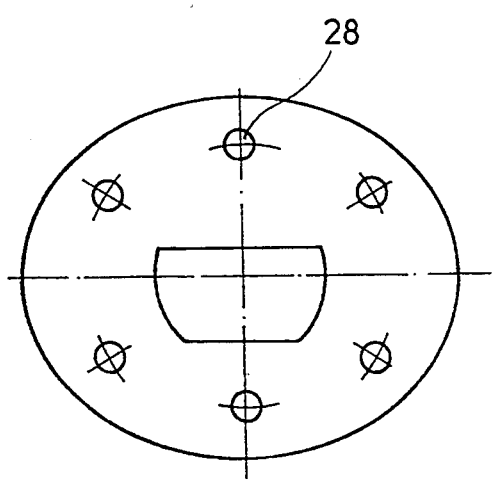
Figure 5:
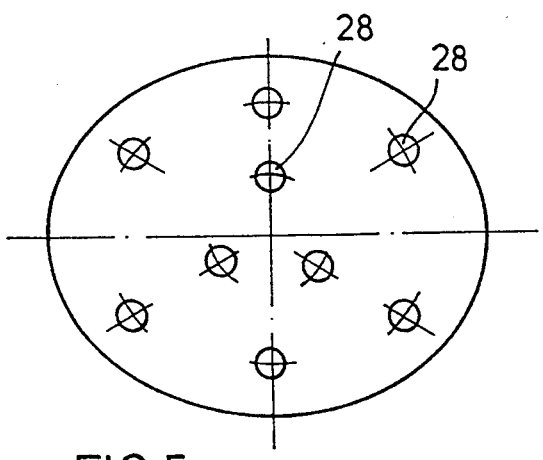

Other advantages and features of the invention will appear from the following description of one non-limiting embodiment with reference to the figures which show:

FIG. 1 a sectional view of a sleeve and bolts including clamping faces;

FIG. 2 a side view of a supporting member shown in an enlarged scale;

FIG. 3 a sectional view of the supporting member along line III—III in FIG. 2;

FIG. 4 a front view of the supporting member facing the clamping means;

FIG. 5 a view of the supporting member facing the vertebra and

Figure 6:
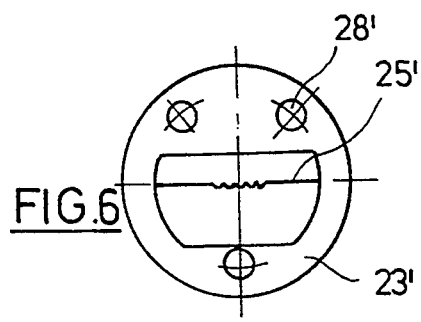

FIG. 6 a view of a different supporting body suited for smaller vertebras.

With reference to FIG. 1 the vertebra spacer comprises a sleeve 1 including internal threads 2 and 3 running opposite to each other, and a relief section 4 of enlarged diameter therebetween.

Bolts 5 and 6 having external thread 7 and 8 are screwed into both ends of the sleeve 1. The bolts are provided with flat faces 9 and 10 which guide discs 11 and 12 including teeth 13 and 14 cooperating with the front faces of the sleeve 1. Counter nuts 15, 16 cooperate with the outer thread 7, 8 of the bolts to fix the discs 11, 12 via the teeth 13, 14 to the sleeve 1 to rigidly secure the bolts 5, 6.

The ends of the bolts 5, 6 bear clamping faces 17, 18 which are provided parallel to the bolts axes and include a toothing 19, 20 at least in segments. The bolt heads forming clamping faces 17 and 18 are further provided with threaded bores 21, 22 to receive screw bolts not shown to mount the supporting members as follows.

According to FIG. 2 the supporting members 23 are provided with a clamping face 25 bearing a toothing 24 which corresponds to the toothing 19 and 20 of the bolt heads. The clamping face 25 extends normal to the supporting face 26 of a supporting plate 27. Pins 28 having rounded ends extend from the face 26 opposite the clamping face 25. As shown in FIG. 3 the pins 28 bear projections 29 which are mounted in bores 30 of the plate 27, for example by being pressed-in.

As shown in FIGS. 2 and 3, the supporting member 23 has a bore 31 to receive a screw bolt to be mounted in the threaded bores 21, 22 of the bolts 5, 6. The head of the screw bolt not shown is tapered and cooperates with a conical portion 32 of the double conical bore 31.

FIGS. 4 and 5 show that the supporting member 26 is oval shaped corresponding to the vertebra shape in the lower region of the vertebral column. Adjacent the edge of the supporting member 26, equally spaced bores 28 in a first ring are provided for a temporary support. A second ring of three equally spaced pins 28 is provided near the center.

According to FIG. 6 a supporting member 23a suited for smaller vertebras in the upper region of the vertebral column has a circular periphery including three equally spaced pins 28a adjacent the edge. The shape of the clamping face 25a corresponds to that of the supporting member 23 to use the clamping faces 17 and 18 of the bolts 5, 6 of the assembly shown in FIG. 1.

A vertebra spacer according to the invention is thus assembled by selecting the desired type of supporting bodies 23 which are then mounted on the premounted sleeve and bolt assembly of FIG. 1. After inserting between a pair of vertebras to be supported, the supporting plates 27 (shown in FIG. 2) are displaced outwardly by rotating the sleeve 1 before aligning the plates until the vertebras are located in the desired distance in the longitudinal direction. Subsequently, the vertebra bodies are adjusted by tilting the supporting plate 27, possibly by some rotation of the bolts 5 and 6. Finally the clamping plates are tightened to the bolts which are secured by tightening the counter nuts 15 and 16 so that a stable and safe support of the vertebra bodies is obtained.

In addition to the spacer system a fixator may be used to fix the vertebral column.

I claim:

1. A spacer device for supporting vertebral bodies, comprising a first substantially plate-shaped supporting member configured to engage a first vertebral body, a second substantially plate-shaped supporting member configured to engage a second vertebral body and an adjustment means including a sleeve having a longitudinal axis and having an internal thread and a pair of bolts having an outer thread cooperating with said sleeve to adjust the supporting members in a predetermined distance with respect to each other, wherein the adjustment means is provided with clamping faces at either end which adjustment faces are aligned with the axis of the sleeve and the bolts or are disposed parallel to said axis, wherein the supporting members are provided with clamping faces extending substantially normally with respect to supporting faces of the supporting member, and wherein a screw connection is provided for each supporting member to press the clamping faces of the adjustment means and the supporting member together in a predetermined position with respect to each other.

2. The spacer device of claim 1, wherein the sleeve cooperates with a pair of bolts, each bolt including a clamping face formed at a free end of each bolt.

3. The spacer device of claim 2, wherein the clamping faces are roughened.

4. The spacer device of claim 2, wherein the clamping faces include a toothing.

5. The spacer device of claim 4, wherein the clamping faces are circular.

6. The spacer device of claim 5, wherein the clamping faces of the supporting members are provided with bores and that the screwing connection includes a screw bolt extending through the bores.

7. The spacer device of claim 6, wherein said screw bolt has a head which is conical cooperating with a conical bore section of the supporting member or, respectively, the threaded bolt.

8. The spacer device of claim 7, wherein the bore of the supporting member is double-conical.

9. The spacer device of claim 8, wherein the screw bolt head is provided with a tool engaging recess.

10. The spacer device of claim 9, wherein the sleeve is provided with flat tool engaging faces.

11. The spacer device of claim 10, wherein a plurality of fixing means cooperating with the bolt and the sleeve are provided to secure said spacer device in axial and rotational position.

12. The spacer device of claim 11, wherein a counter nut is provided on the thread of the bolts.

13. The spacer device of claim 12, wherein the thread of the bolts each include at least a flat face and a disc non-rotatably supported on the flat sides is placed on the bolt between the counter nut and the sleeve, which disc includes a front-sided toothing cooperating with a front face of the sleeve.

14. The spacer device of claim 13, wherein the supporting faces are rounded.

15. The spacer device of claim 13, wherein the supporting faces are oval shaped.

16. The spacer device of claim 15, wherein the supporting members are provided with pins extending beyond the supporting surfaces.

17. The spacer device of claim 16, wherein each supporting member is provided with a plurality of pins near an edge and/or a center of the supporting face.

18. The spacer device of claim 17, wherein each pin has a free end and is rounded at said free end.

19. A spacer device for supporting vertebral bodies, said device comprising:

(a) a first substantially plate-shaped supporting member having a first supporting surface configured to engage a first vertebral body, (b) a second substantially plate-shaped supporting member having a second supporting surface configured to engage a second vertebral body, wherein said first supporting member and said second supporting member are spaced apart at a distance X, and (c) an adjustment means for adjusting said distance X between said first supporting member and said second supporting member, comprising (1) a sleeve having an axis and an internal thread and (2) a pair of bolts, each bolt having an outer thread cooperating with said internal thread of said sleeve, wherein said adjustment means has a first clamping face at a first end thereof and a second clamping face at a second end thereof, wherein said first clamping face and said second clamping face are aligned either coaxially with said axis of said sleeve or are aligned parallel to said axis, wherein said first supporting member has a first clamping face extending substantially normal to said first supporting surface and said second supporting member has a second clamping face extending substantially normal to said second supporting surface, wherein said first supporting member has a first screw connection serving to press said first clamping face and said first supporting member together at a first predetermined position and said second supporting member has a second screw connection serving to press said second clamping face and said second supporting member together at a second predetermined position.

20. A vertebral implant comprising a main body substantially in the shape of a vertebral disc, said main body having
    (a) a curved substantially cylindrical outer surface,
    (b) a substantially flat upper surface and a substantially flat lower surface in a shape selected from the group consisting of circular and oval,
    (c) at least two prongs located on at least one surface selected from the group consisting of said upper surface and said lower surface, and
    (d) a toothed flat face positioned at said curved substantially cylindrical outer surface and positioned substantially perpendicular to said substantially flat upper surface.

21. An implant according to claim 20 and including also a turnbuckle having a first toothed flat turnbuckle face and a second toothed flat turnbuckle face each turnbuckle face configured to engage and be locked to a toothed flat face of an implant according to claim 20.

22. An implant according to claim 21 and including also locking means for locking together a toothed flat turnbuckle face with a toothed flat face of an implant according to claim 20.

* * * * *